US007530353B2

(12) United States Patent
Choncholas et al.

(10) Patent No.: US 7,530,353 B2
(45) Date of Patent: May 12, 2009

(54) APPARATUS AND METHOD FOR DETERMINING AND DISPLAYING FUNCTIONAL RESIDUAL CAPACITY DATA AND RELATED PARAMETERS OF VENTILATED PATIENTS

(75) Inventors: Gary J. Choncholas, Madison, WI (US); Barbara M. Gosenheimer, Lake Mills, WI (US); Paul Michell, Monona, WI (US)

(73) Assignee: The General Electric Company, Schenectady, NY (US)

( * ) Notice: Subject to any disclaimer, the term of this patent is extended or adjusted under 35 U.S.C. 154(b) by 139 days.

(21) Appl. No.: 11/358,855

(22) Filed: Feb. 21, 2006

(65) Prior Publication Data

US 2007/0062529 A1     Mar. 22, 2007

Related U.S. Application Data

(60) Provisional application No. 60/719,322, filed on Sep. 21, 2005.

(51) Int. Cl.
*A61M 11/00*     (2006.01)
(52) U.S. Cl. .............................. 128/204.18; 128/204.23
(58) Field of Classification Search ............ 128/204.18, 128/200.26, 204.22, 204.23, 200.15; 600/532, 600/529
See application file for complete search history.

(56) References Cited

U.S. PATENT DOCUMENTS

| | | | |
|---|---|---|---|
| 5,088,332 A | 2/1992 | Merilianen et al. | |
| 5,540,233 A | 7/1996 | Larsson et al. | |
| 5,915,381 A | 6/1999 | Nord | |
| 5,957,128 A | 9/1999 | Hecker et al. | |
| 6,139,506 A | 10/2000 | Heinonen | |

(Continued)

FOREIGN PATENT DOCUMENTS

EP     0 653 183     5/1995

(Continued)

OTHER PUBLICATIONS

The Nitrogen-Washout Method for Measuring FRC, The Biomedical Engineering Handbook, CRC Press, 1995, ISBN 0-8493-8346-3, pp. 1237-1238.

(Continued)

*Primary Examiner*—Steven O Douglas
(74) *Attorney, Agent, or Firm*—Andrus, Sceales, Starke & Sawall, LLP

(57) ABSTRACT

A ventilator for ventilating a patient has means integrated therewith for carrying out a determination of the functional residual capacity of the patient using an inert gas wash in/wash out technique. To this end, the ventilator operates to alter the inert gas content of breathing gases provided to the patient. The amount of inert gas expired by the patient is obtained and used to determine functional residual capacity on a breath-by-breath basis. A graph of the functional residual capacities for a given number of breaths is produced. Thereafter, the inert gas levels in the breathing gases are returned to the original levels and further functional residual capacity determinations and a graph of same provided. The functional residual capacity information may also be provided in tabular form. A log of functional residual capacity determinations and ventilator settings or patient treatments affecting same may also be provided.

53 Claims, 10 Drawing Sheets

U.S. PATENT DOCUMENTS

| | | |
|---|---|---|
| 6,273,855 B1 * | 8/2001 | Schmid et al. ............... 600/300 |
| 6,315,739 B1 | 11/2001 | Merilainen et al. |
| 6,709,405 B2 | 3/2004 | Jonson |
| 2004/0003813 A1 | 1/2004 | Banner et al. |

FOREIGN PATENT DOCUMENTS

| | | |
|---|---|---|
| EP | 0 791 327 | 8/1997 |
| EP | 791327 | 8/1997 |

OTHER PUBLICATIONS

Automated sulfur hexafluoride washout functional residual capacity measurement system for any mode of mechanical ventilation as well as spontaneous respiration, Thomas D. East, Ph.D. et al., Critical Care Medicine, vol. 18, No. 1, 1990, pp. 8491.

Determination of Lung Volume in the ICU, H. Burchardi, et al., Yearbook of Intensive Care and Emergency Medicine, 1998, ISBN 3-540-63798-2, pp. 353-360.

Practical Assessment of Respiratory Mechanics, W. Stenqvist, British Journal of Anaesthesia 91 (1): 92-105 (2003).

The Dynostatic Algorithm in Adult Paediatric Respiratory Monitoring, Soren Sondergaard, Thesis, University Hospital, Gothenburg University, Sweden (2002). (Summary).

A Simple Method to Estimate Functional Residual Capacity in Mechanically Ventilated Patients, R. Fretschner et al., Intensive Care Medicine (1993) 19:372-376.

The Recording of FRC—Is it of Importance and Can It Be Made Simple?; G. Hedenstierna; Intensive Care Medicine (1993) 19:365-366.

Estimation of Functional Residual Capacity at the Bedside Using Standard Monitoring Equipment: A Modifiec Nitrogren Washout/Washin Technique Requiring a Small Change of the Inspired Oxygen Fraction; C. Olegard et al. Aneseth Analg. (2005)101:206-12.

Partial European Search Report dated Feb. 24, 2009.

* cited by examiner

APPARATUS AND METHOD FOR DETERMINING AND DISPLAYING FUNCTIONAL RESIDUAL CAPACITY DATA AND RELATED PARAMETERS OF VENTILATED PATIENTS

CROSS REFERENCE TO RELATED APPLICATION

The present application claims the priority of U.S. Provisional Application No. 60/719,322, filed Sep. 21, 2005.

BACKGROUND AND SUMMARY

The present invention relates to an apparatus and method for determining and displaying functional residual capacity data and other pulmonary parameters, such as positive end expiratory pressure (PEEP) data, for patients breathing with the aid of a mechanical ventilator, such as a critical care ventilator. The invention also determines and displays relationships between these and other parameters.

Functional residual capacity (FRC) is the gas volume remaining in the lungs after unforced expiration or exhalation. Several methods are currently used to measure functional residual capacity. In the body plethysmography technique, the patient is placed in a gas tight body box. The patient's airway is sealingly connected to a breathing gas conduit connected to the exterior of the body box. By measuring lung pressures and pressures in the box, at various respiratory states and breathing gas valve flow control conditions, the functional residual capacity of the patient can be determined.

Another technique for measuring functional residual capacity is the helium dilution technique. This is a closed circuit method in which the patient inhales from a source of helium of known concentration and volume. When the concentration of helium in the source and in the lungs has reached equilibrium, the resulting helium concentration can be used to determine the functional residual capacity of the patient's lungs.

A further technique for determining functional residual capacity is the inert gas wash-out technique. This technique is based on a determination of the amount of gas exhaled from the patient's lungs and corresponding changes in gas concentrations in the exhaled gas. The gas used for the measurement is inert in the sense that it is not consumed by metabolic activity during respiration. While a number of gases may be used for such a measurement of functional residual capacity, it is convenient to use nitrogen for this purpose.

In a straightforward example in which the patient is initially breathing air, the lung volume forming the functional residual capacity of the lung will contain nitrogen in the same percentage as air, i.e. approximately 80%, the remaining 20% of air being oxygen. In a wash-out measurement, the subject commences breathing gases in which oxygen is at a different concentration than 20%. For example, the patient commences breathing pure oxygen. With each breath, nitrogen in the lungs is replaced by oxygen, or, stated conversely, the nitrogen is "washed out" of the lungs by the oxygen. While the breathing of pure oxygen could continue until all nitrogen is washed out of the lungs, in most cases, the breathing of oxygen continues until the nitrogen concentration in the exhaled breathing gases falls below a given concentration. By determining the volume of inert gas washed out of the lungs, and knowing the initial concentration of the inert gas in the lungs, the functional residual capacity of the lungs may be determined from these quantities.

Methods for determining functional residual capacity in this manner are well known and are described in such literature as The Biomedical Engineering Handbook, CRC Press, 1995, ISBN 0-8493-8346-3, pp. 1237-1238, Critical Care Medicine, Vol. 18, No. 1, 1990, pp. 8491, and the Yearbook of Intensive Care and Emergency Medicine, Springler, 1998, ISBN 3-540-63798-2, pp. 353-360. By analogy to the above described wash out measurement technique, it is also possible to use a wash in of inert gas for measurement of functional residual capacity. Such a method and apparatus is described in European Patent Publication EP 791,327.

The foregoing methods are used with spontaneously breathing patients and are typically carried out in a respiratory mechanics laboratory. But in many cases, patients that could benefit from a determination of functional residual capacity are so seriously ill as to not be breathing spontaneously but by means of a mechanical ventilator, such as a critical care ventilator. This circumstance has heretofore proven to be a significant impediment in obtaining functional residual capacity information from such patients. Additionally, the patient's illness may also make it impossible or inadvisable to move the patient to a laboratory or into and out of a body box for the determination of functional residual capacity.

It would therefore be highly advantageous to have an apparatus and method by which the functional residual capacity of mechanically ventilated patients could be determined. It would be further advantageous to associate the apparatus for carrying out the determination of functional residual capacity with the ventilator to reduce the amount of equipment surrounding the patient and to facilitate set up and operation of the equipment by an attending clinician. Such apparatus would also enable the determination of functional residual capacity to be carried out at the bedside of the patient, thus avoiding the need to move the patient.

A single determination of functional residual capacity provides important information regarding the pulmonary state of the patient. However, it is often highly desirable from a diagnostic or therapeutic standpoint to have available trends or changes in the functional residual capacity of a patient over time.

It would also be helpful to be able to relate functional residual capacity to other pulmonary conditions existing in the lungs or established by the ventilator and to changes in these conditions. For example, it is known that the pressure established by the ventilator in the lungs at the end of expiration, the positive end expiratory pressure or PEEP, affects the functional residual capacity of the lungs.

Typically, an increase in PEEP increases functional residual capacity. There are two components to the increased functional residual capacity as PEEP is increased. One component is due to stretching of the lung by the increased pressure. A second component, particularly in diseased lungs, occurs from the effect of PEEP during breathing by the patient. As a patient expires, the pressure in the lungs drops until it approaches airway pressure. As the pressure within the lungs drops, the alveoli or air sacs in the lungs deflate. If alveolar sacs collapse completely, more pressure is required upon inspiration to overcome the alveolar resistance and re-inflate the alveolar sacs. If this resistance cannot be overcome, the volume of such sacs are not included in the functional residual capacity of the patient's lungs.

By applying PEEP in the patient's airway, the additional pressure in the patient's lungs keeps more of these alveolar sacs from completely collapsing upon expiration and, as such, allows them to participate in ventilation. This increases the functional residual capacity of the patient's lungs and the increase is often described as "recruited volume." Volume reductions are termed "de-recruitments."

However, setting the PEEP too high can cause excessive lung distension. There may also be compression of the pulmonary bed of the lung, loading the right side of the heart and reducing the blood volume available for gas exchange. Either of these circumstances present the possibility of adverse consequences to the patient.

Still further, action such as performing a suction routine, administering a nebulized medication, or changing the ventilation parameters of the ventilator can also influence functional residual capacity and it would be helpful to be able to easily determine the effect of such actions on functional residual capacity.

An apparatus and method that would possess the foregoing characteristics and that would easily and cogently make such information available would be highly beneficial in conveniently obtaining a full understanding of the pulmonary condition of the patient and how the patient is reacting to the mechanical ventilation and to any associated therapeutic measures. The clinician could then carry out appropriate action beneficial to the patient in a timely and informed manner.

BRIEF DESCRIPTION OF THE PRESENT INVENTION

An embodiment of the present invention comprises an apparatus and method that achieves the desired, highly advantageous features noted above. Thus, with the present invention the functional residual capacity of a mechanically ventilated patient may be determined at the bedside of the patient without the need to move the patient to a laboratory. By associating the apparatus with the ventilator, only a single device need be employed to both ventilate the patient and determine functional residual capacity.

The determined functional residual capacity may be advantageously displayed in conjunction with earlier determinations and in conjunction with other pulmonary conditions, such as PEEP. Changes, or trends, in functional residual capacity over time may thus be discerned, along with changes in the other pulmonary conditions.

Additionally, the apparatus and method provides a log of events having the potential to impact the functional residual capacity of the patient and/or its accurate determination. Such events may include suctioning the patient, administering a nebulized medication to the patient, performing a lung recruitment maneuver, and altering the PEEP or other ventilator parameters. The apparatus may also automate functional residual capacity measurement in conjunction with these types of events. For example, it is desirable to provide that functional residual capacity measurements be automatically conducted immediately before and after nebulized drug therapy in order to precisely gauge the effect of the nebulization treatment.

The foregoing provides an attending clinician with significant information for assessing the state of, and trends in, the functional residual capacity of the patient, as well as the relationship between the patient's residual capacity and the other factors, so that the clinician can fully discern the functional residual capacity condition of the patient.

Further features of the apparatus and method of the present invention will be apparent from the following detailed description, taken in conjunction with the associated drawing.

DETAILED DESCRIPTION

The Mechanical Ventilator and Airway Gas Module

Figure 1:
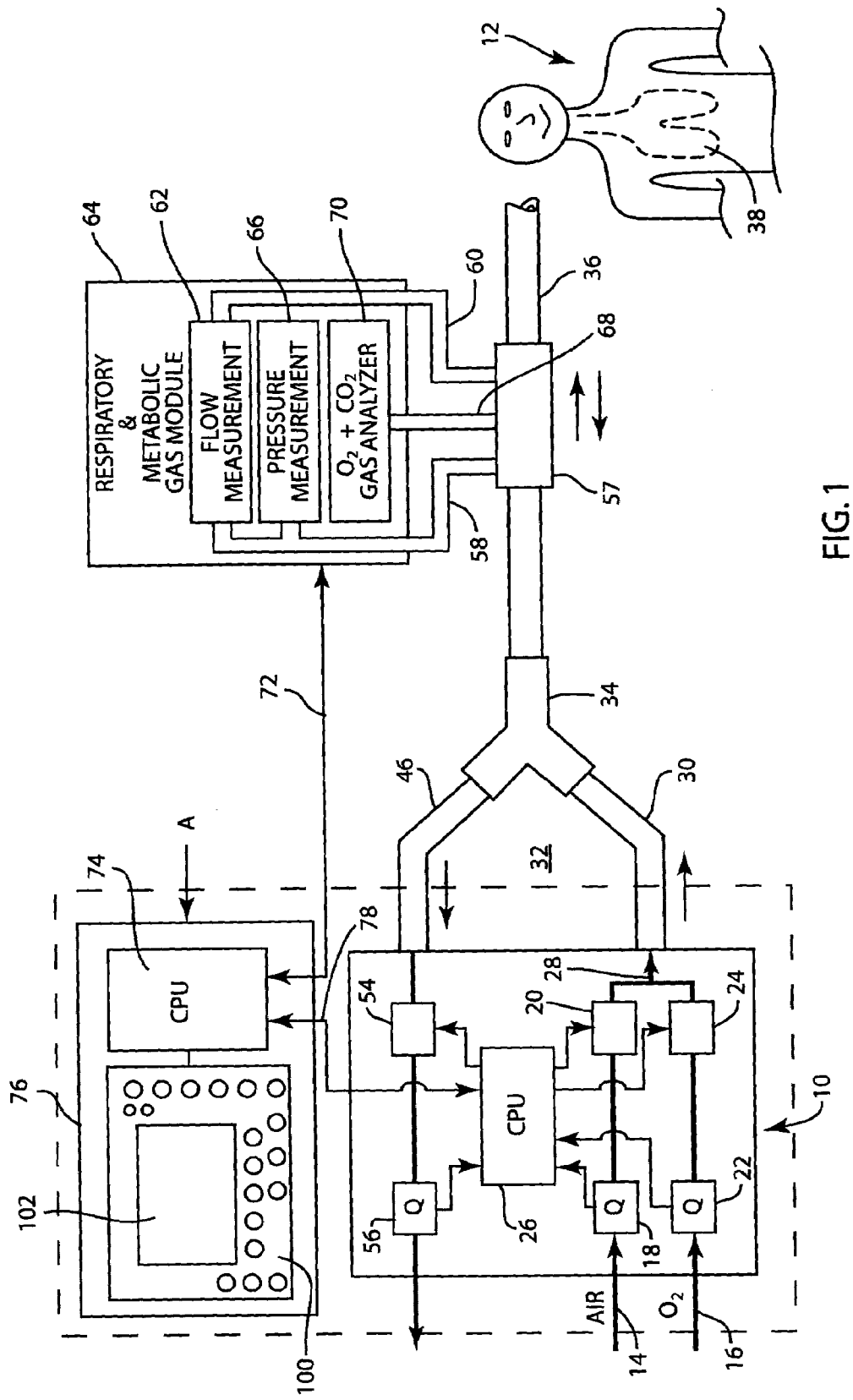
FIG. 1 is a general diagram of a mechanical ventilator and associated apparatus for ventilating a patient.

FIG. 1 shows mechanical ventilator 10 for providing breathing gases to patient 12. Ventilator 10 receives air in conduit 14 from an appropriate source, not shown, such as a cylinder of pressurized air or a hospital air supply manifold. Ventilator 10 also receives pressurized oxygen in conduit 16 also from an appropriate source, not shown, such as a cylinder or manifold. The flow of air in ventilator 10 is measured by flow sensor 18 and controlled by valve 20. The flow of oxygen is measured by flow sensor 22 and controlled by valve 24. The operation of valves 20 and 24 is established by a control device such as central processing unit 26 in the ventilator.

The air and oxygen are mixed in conduit 28 of ventilator 10 and provided to inspiratory limb 30 of breathing circuit 32. Inspiratory limb 30 is connected to one arm of Y-connector 34. Another arm of Y-connector 34 is connected to patient limb 36. During inspiration, patient limb 36 provides breathing gases to lungs 38 of patient 12. Patient limb 36 receives breathing gases from the lungs of the patient during expiration. Patient limb 36 may include components such as a humidifier for the breathing gases, a heater for the breathing gases, a nebulizer, or a water trap (not shown). The breathing gases expired by patient 12 are provided through patient limb 36 and Y-connector 34 to expiratory limb 46 of breathing circuit 32. The expired breathing gases in expiratory limb 46 are provided through valve 54 and flow sensor 56 for discharge from ventilator 10. Valve 54 may be used to establish the PEEP for patient 12.

Patient limb 36 includes gas flow and pressure sensor 57 which may be of the type shown in U.S. Pat. No. 5,088,332. A pair of pressure ports and lines 58, 60 are placed on either side of a flow restriction in the sensor and the pressure difference developed across the flow restriction is used by flow measurement unit 62 in gas module 64 to measure gas flow in patient limb 36. One of the pressure lines is connected to pressure measurement unit 66 to measure the pressure in patient limb 36. Sensor 57 also provides for a gas sampling line 68 which is connected to gas analyzer 70. Gas analyzer 70 may measure the amount of oxygen and carbon dioxide in the breathing gases. Knowing the amounts of oxygen and carbon dioxide in the breathing gases enables the amount of nitrogen to be determined as the total amount of breathing gas less the amounts of carbon dioxide and oxygen. Respiratory and metabolic gas module 64 may comprise that made and sold by GE Healthcare as a Datex-Ohmeda MCOVX gas module. The output of gas module 64 is provided in data bus 72 to central processing unit 74 in ventilator display unit 76. Central processing unit 26 in ventilator 10 is also connected to central processing unit 74 via data bus 78.

The Endotracheal Tube

Figure 2:
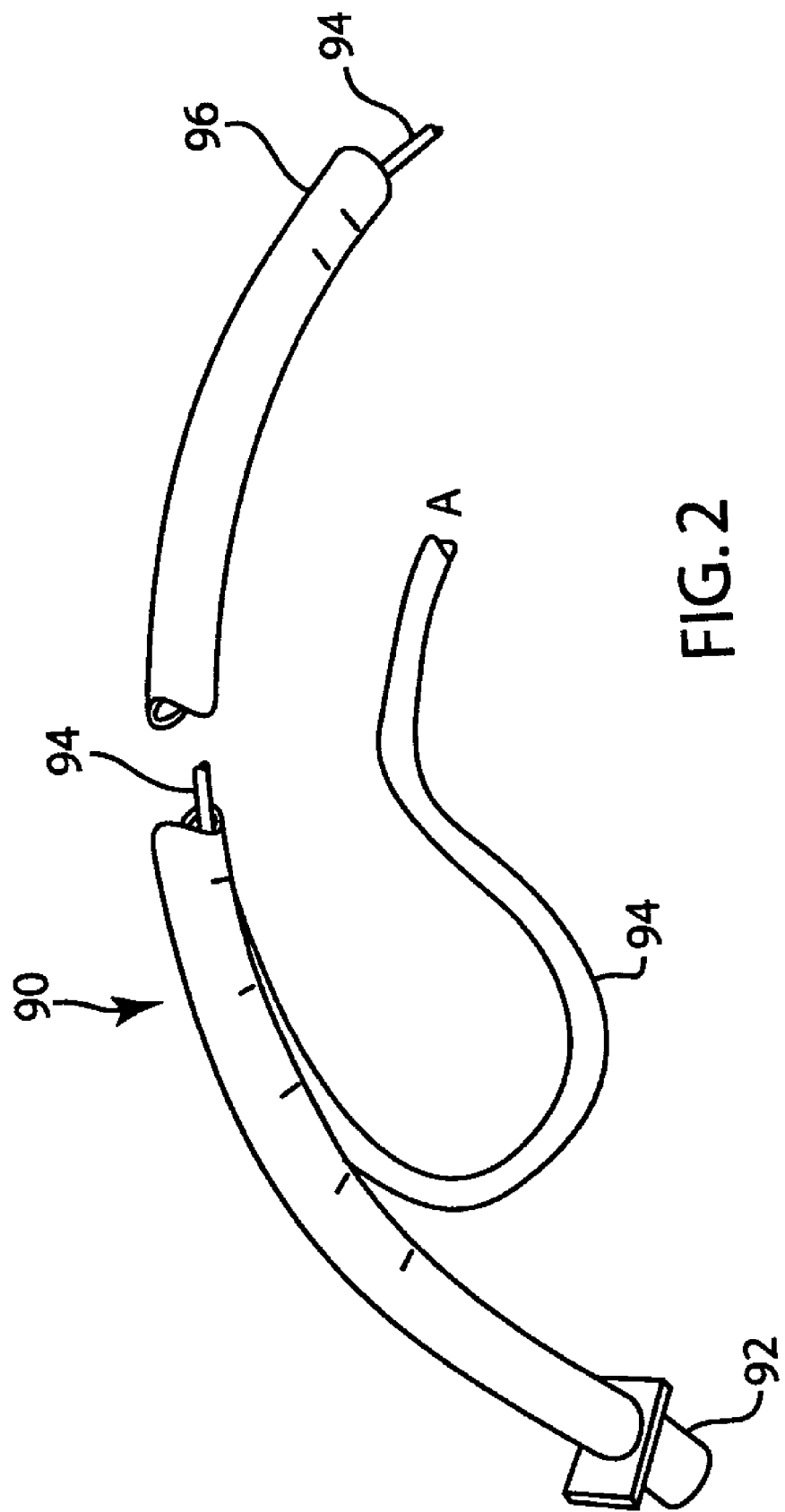
FIG. 2 shows an endotracheal tube with a tracheal pressure sensor suitable for use in the present invention.

To obtain an accurate indication of the pressure in lungs 38 of the patient 12, endotracheal tube 90 shown in FIG. 2 may be used. Endotracheal tube 90 has end 92 for connection to patient limb 36. In use, endotracheal tube 90 extends through the mouth and into the trachea of patient 12 to provide an airway passage to lungs 38.

Endotracheal tube 90 includes pressure sensor catheter 94 that extends from end 96 to provide a pressure sampling point that is close to lungs 38 of patient 12 when the endotracheal tube is inserted in the patient and can thus obtain a highly accurate indication of the pressure in the lungs. An intermediate portion of catheter 94 may lie within endotracheal tube 90. The proximal portion exits the endotracheal tube and is connected via A-A to a pressure transducer and to an auxiliary input to ventilator display unit 76. The pressure obtained from catheter 94 is termed Paux. While FIGS. 1 and 2 show a connection to ventilator display unit 76 for this purpose, the connection may, alternatively, be to gas module 64.

An endotracheal tube of the type shown in FIG. 2 is described in U.S. Pat. No. 6,315,739.

Ventilator Display Unit

Display unit 76 of ventilator 10 receives information from the ventilator and gas module 64 and is used by the clinician to control, via data bus 78, the pneumatic control components of ventilator 10 that deliver breathing gases to patient 12. Additionally, central processing unit 74 in display unit 76 carries out the determination of functional residual capacity, recruited/de-recruited volumes, and other quantities employed in the present invention. It will be appreciated that other CPU configurations, such as a single CPU for the ventilator and its display unit may be used, if desired.

Ventilator display unit 76 includes user interface 100 and display 102. Display 102 is shown in greater detail in FIG. 3. Display 102 is divided into a number of display portions 102a-g for displaying inputted, sensed, and computed information. Display portions 102a through 102f relate primarily to the operation of ventilator 10 and the ventilation of patient 12 and are discussed briefly below. Display screen portion 102g displays information and relationships in accordance with the present invention, as described in detail below.

Display portion 102a provides for the display of operating information of ventilator 10. The portion shows the type of ventilation being performed by ventilator 10, in the exemplary case of FIG. 3, synchronized, intermittent, mandatory ventilation, or SIMV-volume controlled ventilation. Portion 102a also provides a display of operating information inputted into ventilator 10 including the percentage of oxygen for the breathing gases, tidal volume (TV), breathing rate, inspiration time ($T_{insp}$), amount of positive end expiratory pressure (PEEP) and the pressure limit ($P_{limit}$) set for the volume controlled ventilation. To input these operating parameters into ventilator 10, an appropriate one of buttons 104a through 104f is actuated. Control knob 106 is rotated to enter a desired value for the selected option and pressed to confirm the new parameter value. Further ventilator functions may be controlled by pressing a button that controls a specialized function such as ventilator setup button 73 that establishes other ventilation modes for patient 12, spirometry button 75 for showing and controlling the display of spirometry information, 100% $O_2$ button 77, nebulizer button 79, and procedures button 80 that controls specialized procedures for ventilator 10.

Display portion 102b of display 102 shows airway pressure data as measured from sensor 57. Portion 102c shows textual information relating to the flow of breathing gases to the patient obtained from sensor 57, and portion 102d shows pressure data from catheter 94 in the endotracheal tube 90 during ventilation of patient 12.

Portion 102e of display 102 shows the information in portions 102b, 102c, and 102d in graphic form and includes an indication of certain other operating information, such as the mode of ventilation SIMV-VC, and whether certain features of the present invention are operational or not.

Figure 3:
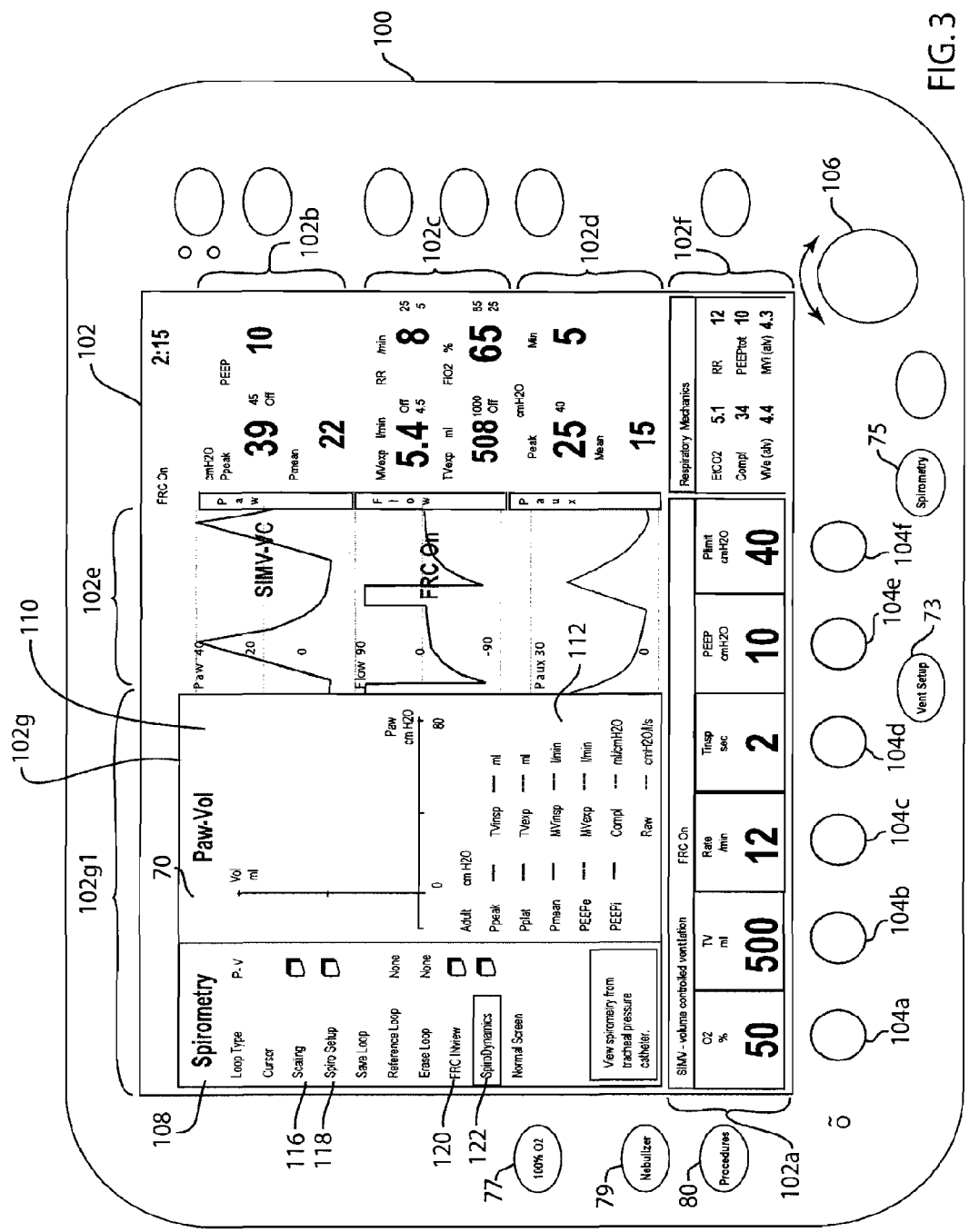
FIG. 3 shows a ventilator display unit presenting an initial display screen for use in the present invention.

Display portion of 102 shows additional data as selected by the clinician. In the example of FIG. 3 end tidal $CO_2$ ($E_tCO_2$), lung compliance, expiratory alveolar minute volume (MVe (alv)), respiratory rate, total positive end expiratory pressure, and inspiratory alveolar minute volume (MVi(alv)) are being shown.

Display portion 102a-f remain generally unchanged as the present invention is practiced although, as noted above, the clinician may select the information to be shown in certain portions, such as portion 102f.

Display Screen of Present Invention

Figure 4:
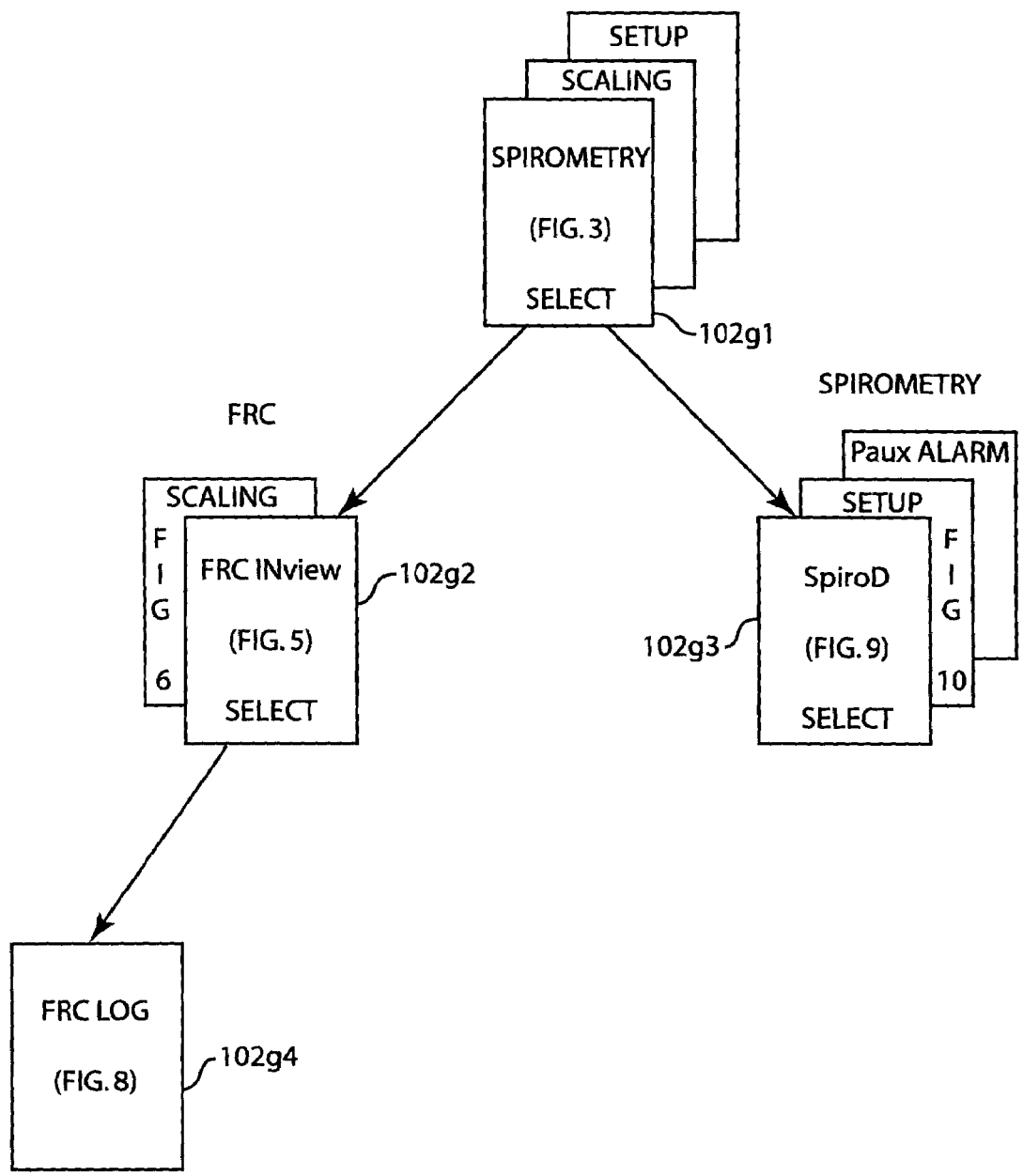
FIG. 4 is a chart showing the relationship among a plurality of screens employed in the present invention.

Display screen 102g is the part of display 102 employed in the present invention. As shown in FIG. 4 and in FIGS. 5, 6, 8, 9, and 10, the content of this screen will change, depending on the inventive feature being utilized, the different content in screen 102g being identified as 102g1, 102g2, 102g3, etc. in the appropriate figures of the drawing.

In general, each screen 102g will include a menu or control portion 108, a graphic portion 110 and tabular portion 112. For this purpose, graphic portion 110 contains a pair of orthogonal axes by which data can be graphically presented. The clinician may navigate and control the screen using control knob 106. Control knob 106 is rotated to scroll through the menu options displayed in menu portion 108, depressed to select a menu option, rotated again to establish a numerical value for the selected option when appropriate, and depressed again to enter the value into ventilator display unit 76 or to confirm selection of the menu option.

FIG. 3 shows an initial content for screen 102g relating to spirometry. As hereinafter noted, spirometry illustrates the relationship between inspired gas volumes and the pressure in the lungs as the patient breathes. The graphic form of the data is normally in a loop, one portion of which is formed during inspiration and the other portion of which is formed during expiration in the manner shown in FIG. 9. The tabular portion 112 provides fields in which various obtained and computed ventilation and lung properties may be displayed.

Menu portion 108 allows the clinician to select a number of options with respect to the display and use of the information shown in graphic and tabular portions 110 and 112. Menu portion 108 also allows the clinician to select a further screen at 116 for adjusting the scaling for the abscissa and ordinate of graph 110 and the setup for spirometry measurements at 118.

From menu portion 108, the clinician may also select screens that allow the functional residual capacity (FRC) features of the present invention and the spirometry features of the present invention to be carried out by selecting items 120 and 122, respectively. The spirometry features of the present invention are identified by applicant as SpiroDynamics or the abbreviation SpiroD.

Figures 9, 10:
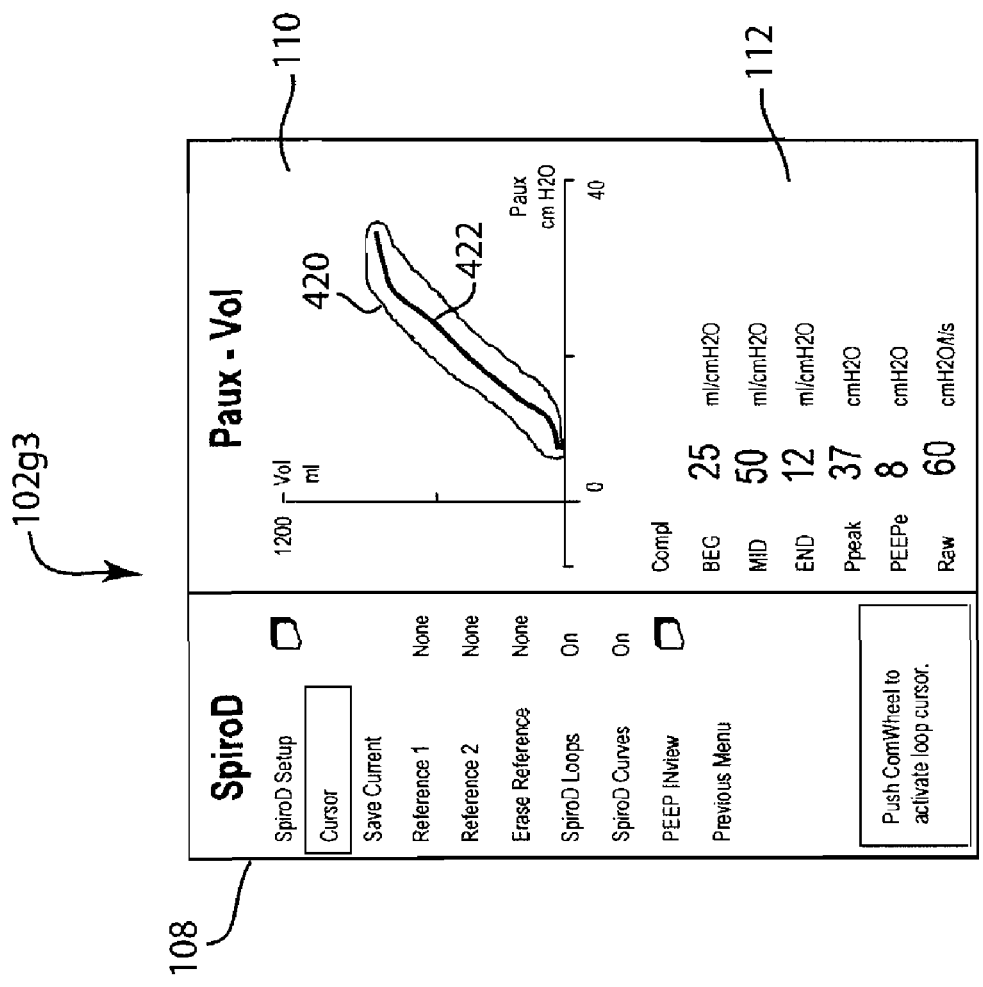
FIG. 9 shows a display showing spirometry data.
FIG. 10 shows a display for making setup adjustments for the screen shown in FIG. 9.

FIG. 4 shows the architecture of the screens 102g used in the present invention. As noted above, the spirometry screen shown in FIG. 3 as screen 102g1 is the initial screen appearing as screen 102g. Also as noted above, associated with this screen are screens for spirometry scaling and spirometry setup By means of menu items 120 and 122, the clinician can select either a screen relating to functional residual capacity, namely screen 102g2 shown FIG. 5 or a screen relating to SpiroDynamics comprising screen 102g3 of FIG. 9. The screen format of FIG. 5 is termed "FRC INview." The view of FIG. 9 is termed "spiroD".

Figure 6:
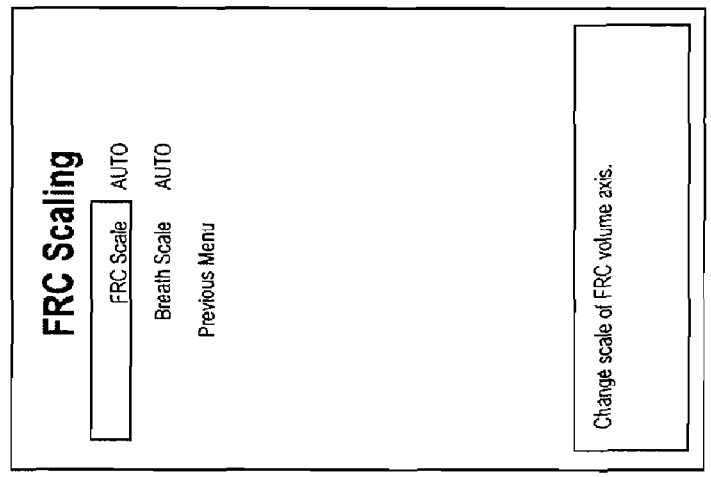
FIG. 6 shows a display for use in scaling the display shown in FIG. 5.
Figure 5:
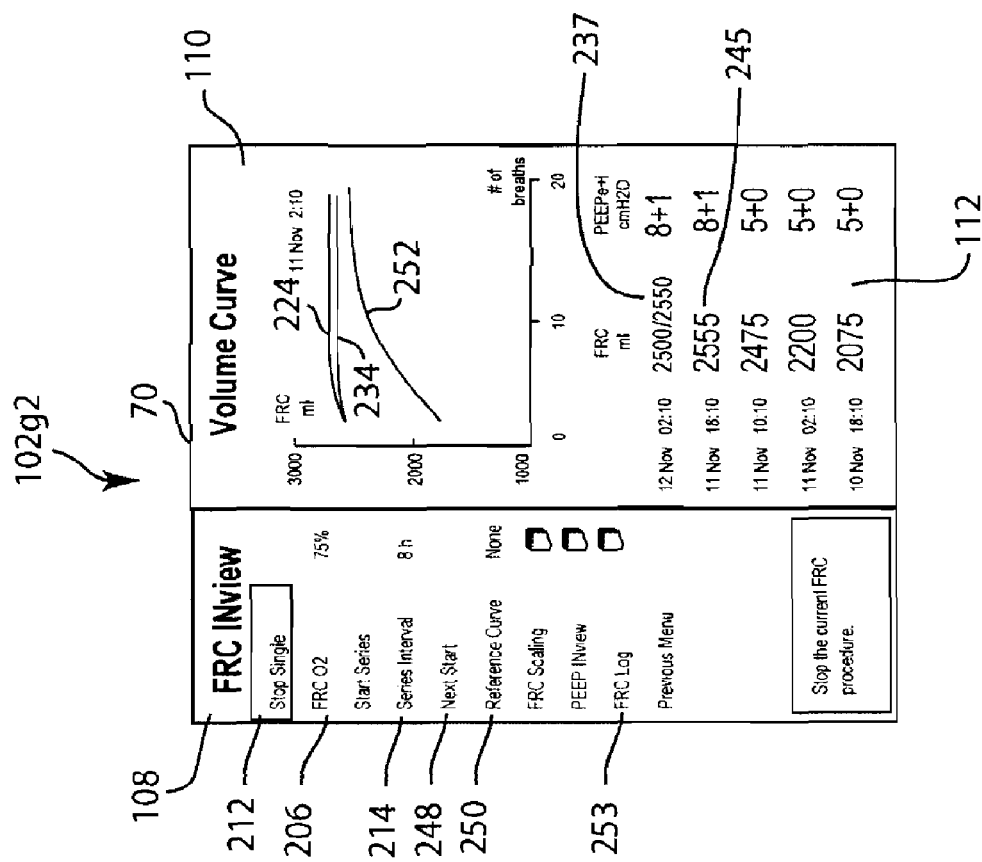
FIG. 5 shows a display screen for displaying functional residual capacity data and related data.

The FRC INview showing of 102g2 includes screen shown in FIG. 6 that allows for scaling of the quantities shown graphically in FIG. 5.

Figure 8:
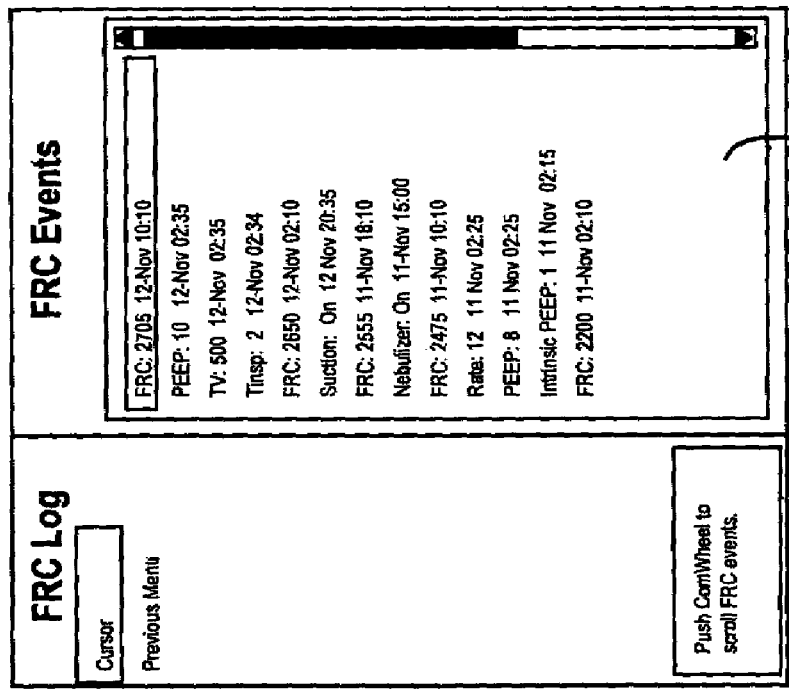
FIG. 8 shows a display displaying a log of events and actions that may impact the determination of functional residual capacity.

A further selection on the FRC INview screen allows the clinician to select the FRC log screen shown in FIG. 8 as screen 102g4.

FRC Determination and Display

Figure 7:
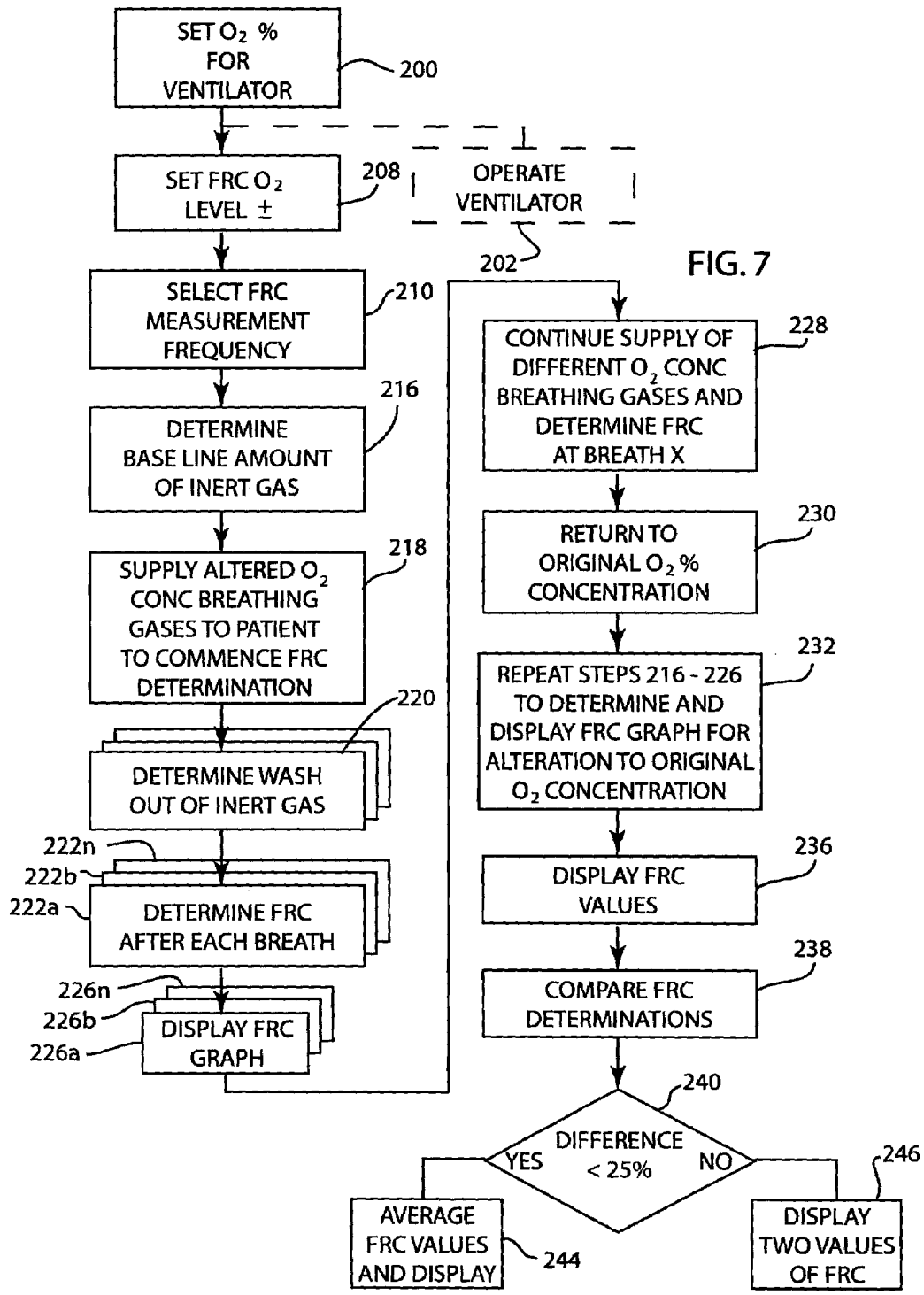
FIG. 7 is a flow chart showing the steps for carrying out a measurement of functional residual capacity in accordance with a method of the present invention.

The flow chart of FIG. 7 shows a method of the present invention for determining and displaying functional residual capacity information for patient 12. The clinician uses a screen in the format of 102g2 of FIG. 5. It is assumed that the clinician has previously established an oxygen percentage for the breathing gases to be provided by ventilator 10 using button 104a, control knob 106 and screen region 102a, at step 200. In the example shown in FIG. 3, the oxygen percentage is 50%. Ventilator 10 can be operated with the set percentage of oxygen to provide breathing gases to patient 12 at step 202.

As noted above, in order to determine the functional residual capacity of patient 12 by a gas wash-out/wash-in technique, it is necessary to alter the composition of the breathing gases supplied to patient 12. To this end, the clinician sets a different level for the oxygen content of the breathing gases. This is performed by selecting the FRC $O_2$ field 206 in menu portion 108 of screen 102g2 and appropriately establishing the FRC $O_2$ value. The amount of change may be an increase or decrease from the previously set level established at step 200; however it must be an amount sufficient to perform the functional residual capacity analysis. A change of at least 10% is preferable in order to obtain an accurate indication of the functional residual capacity. To ensure that appropriate oxygen concentrations are supplied to patient 12 it is usually desired to increase the oxygen level and, unless the current oxygen level is very high (greater than 90%), a default setting of a 10% increase over the current setting may be provided. The level of oxygen set by the clinician "tracks" changes made in the oxygen content of the breathing gases at the ventilator, as for example by actuating button 104a. Thus, for example, if the ventilator oxygen is originally 50% as shown in FIG. 3, and the FRC 02 shown in FIG. 5 is 60%, if the ventilator oxygen setting is later changed to 70%, the FRC 02 amount will automatically move to 80%. Lowering the ventilator oxygen setting, however, will not result in lowering the FRC 02 amount, thereby avoiding the possibility of low oxygen breathing gases for the patient. The alteration of the oxygen content of the breathing gases is carried out in step 208 of FIG. 7. For exemplary purposes, below, an alteration in the form of an increase to 75% $O_2$ is shown in FIG. 5.

Next, the clinician must select the frequency, or interval, at which the functional residual capacity measurements will be carried out. This is performed at step 210. A single functional residual capacity determination by the present method may be selected by the appropriate field 212 in menu 108. Alternatively, a series of FRC determinations or cycles may be selected, with a series interval, set in field 214, between each determination. The interval is typically between one and twelve hours in increments of one hour but may be more frequent. The time when the next functional residual capacity determination begins is shown in field 248.

Alternatively, functional residual capacity measurements can be set to occur automatically in conjunction with certain procedures controlled by ventilator 10, such as immediately prior and/or after a period of nebulized drug therapy, recruitment maneuvers, a suction procedure, or a change in ventilator setting. Functional residual capacity measurement may be initiated, terminated, delayed, interrupted, or prevented in accordance with the occurrence of events, such as those noted above, that may affect the accuracy of the functional residual capacity measurement. For example, a functional residual capacity measurement may be terminated for a high oxygen procedure for patient 12 and then resumed or started after a "lock out" period.

The initial or base line amount of nitrogen in the expired breathing gases is determined at step 216. As noted above this may be determined by subtracting the amounts of oxygen and carbon dioxide, as determined by gas analyzer 70, from the total amount of the breathing gases, as determined using flow measurement unit 62.

While the present invention is described using nitrogen as the inert gas, it will be appreciated that other inert gas may also be used. For example, the breathing gases for patient 12 may include the inert gas helium and amounts of helium expired by the patient could be used in a functional residual capacity measure in the manner described herein.

To commence the determination of functional residual capacity, breathing gases having the increased amount of oxygen shown in data field 206 are provided to patient 12 in step 218. The increased percentage of oxygen in the breathing gases will wash a portion of the nitrogen or other inert gas out of lungs 38 of patient 12 with each breath of the patient. The amount of breathing gases inspired and expired by patient 12 with each breath, i.e. the tidal volume, is a lung volume that is in addition to the residual volume of the lungs found after expiration. The tidal volume is also smaller than the residual volume. For a healthy adult a typical tidal volume is 400-700 ml whereas the residual volume or functional residual capacity is about 2000 ml. Therefore, only a portion of the nitrogen in the lungs 38 of patient 12 is replaced by the increased amount of oxygen with each breath.

The amount of nitrogen washed out of the lungs in each breath is determined by subtracting the amount of oxygen and carbon dioxide from the amount of breathing gases expired by patient 12 during each breath obtained using flow measurement unit 62. See step 220. Knowing the amounts of expired breathing gases, the initial amount of expired nitrogen and the amount expired in each expiration by patient 12, a functional residual capacity quantity can be determined for each successive breath in steps 222*a*, 222*b* . . . 222*n*. Any inert gas wash out/wash in functional residual capacity measurement technique may be used, a suitable technique for determining functional residual capacity for use in the present invention being described in U.S. Pat. No. 6,139,506.

The functional residual capacity quantity as determined after each successive breath, will tend to increase as nitrogen continues to be washed out of the lungs of the patient by the increased oxygen in the breathing gases. This results from the fact that the breathing gases that are inspired by patient 12, i.e., the tidal volume, are not fully equilibrated inside the entire functional residual capacity volume before being exhaled by the patient. In particular, functional residual capacity volume that lies behind intrinsic lung resistance does not mix as quickly with inspired gases compared to functional residual capacity volume that is pneumatically connected to the trachea through a lower resistance path. As such, the magnitude of breath-to-breath increases in functional residual capacity that are noted are an indication of the amount of intrinsic resistance within the lung gas transfer pathways. Thought of another way, additional functional residual capacity volume that is registered many breaths into the functional residual capacity measurement procedure is lung volume that is not participating well in the gas transfer process.

As the determination of functional residual capacity proceeds, the determined values for functional residual capacity for the breaths are displayed in graphic portion 110 of screen 102*g*2 as a capacity or volume curve 224 in steps 226*a*, 226*b* . . . 226*c* at the end of the determination for each breath. This confirms to the clinician that the determination of functional residual capacity is working properly. Also, as curve 224 forms from left to right, the shape of the curve is an indication to the clinician of the intrinsic resistance and quality of ventilation of lung functional residual capacity, as discussed above. In the example shown, the clinician can appreciate that patient 12 has a homogeneously ventilated lung volume, as indicated by the qualitative flatness of the functional residual capacity curve, with a lung residual capacity of about 2500 ml.

The scaling of graph 110 of FIG. 5 may be automatically altered to provide a scale appropriate to the fictional residual capacity data being shown.

It will be appreciated that, if desired, the data relating breath number to the corresponding functional residual capacity value can also be displayed in tabular form in the display of ventilator display unit 76. This could comprise a column containing the breath numbers and a column containing the corresponding functional residual capacity values.

Mechanical ventilator 10 continues to supply breathing gases having increased oxygen concentration for x number of breaths, for example, 20 breaths. A final value for functional residual capacity is determined at the end of the x breaths at step 228 and volume or capacity curve 224 extends to this breath to show the final determination of functional residual capacity at the end of 20 breaths.

Thereafter, at step 230 the concentration of oxygen in the breathing gases is altered to the original level of, for example 50%, set at step 200 and ventilator 10 is operated at step 232 to repeat steps 216-228 to make a second determination of functional residual capacity with this alteration of the oxygen concentration in the breathing gases. It will be appreciated that this determination uses a wash-in of nitrogen, rather than a wash-out. This second determination is graphed and displayed in graphic portion 110 as graph 234, in the same manner as graph 224, described above. The values for the two final functional residual capacity determinations are shown in data field 237 of tabular portion 112 of screen 102*g*2 in step 236. In the example shown, these values are 2500 and 2550 ml.

For future use, the final determination of functional residual capacity made in step 232 is compared to that determined in step 228. This is carried out at step 238. It is then determined, in step 240, whether the difference between the two determinations of functional residual capacity is less or greater than some amount, such as 25%. If the difference is less than 25%, the two values are averaged and will be subsequently displayed in text form in data field 245 in step 244 when the determination becomes part of the chronological record following a later functional residual capacity determination.

If the difference between the two values for the functional residual capacity is greater than some amount, such as than 25%, both the final value determined at step 228 and the final value determined in step 232 will be displayed by step 246 in data field 245 of FIG. 5 and in the graph 110. This display of the functional residual capacity determination informs the clinician that the accuracy of the functional residual capacity determination is questionable.

The final value(s) for the functional residual capacity are preferably displayed in tabular portion 112 of screen 102*g*2 along with additional associated data such as the time and date at which functional residual capacity was determined, or the values of PEEPe and PEEPi existing when the functional residual capacity determination was made. PEEPe is the end expiratory pressure established by ventilator 10. PEEPi, also known as auto PEEP, is the intrinsic end expiratory pressure and is a measurement in pressure of the volume of gas trapped in the lungs at the end of expiration to the PEEPe level.

While the determination of functional residual capacity has been described as being carried out for a given number of breaths, such as 20, it can be terminated sooner if it is apparent that the functional residual capacity measurement has become stable on a breath-to-breath basis. This can be conveniently determined by measuring the $O_2$ content of the expired breathing gases at the end of the patient's expirations, that is, the end tidal oxygen level. When the amount of oxygen in the expired breathing gases remains unchanged for a predetermined number of breaths, it is an indication that the wash out/wash in the inert gas is complete and that the functional residual capacity determination can be terminated.

Thereafter, if a series of functional residual capacity determinations has been selected at step 210, steps 218 through 246 are repeated after the time interval indicated in data field 214 with the start of the functional residual capacity determination occurring at the time displayed in data field 248. The predetermined time interval may be overridden or the functional residual capacity determination terminated by appropriate commands from the clinician entered into menu 108.

The volume curves, such as 224, 234, and functional residual capacity data, such as that in field 237, generated in the course of successive functional residual capacity determinations are saved by ventilator display unit 76 and, as such, can be compared to data from previous or subsequent functional residual capacity determinations. This comparison requires that a previous determination of functional residual capacity be selected as a reference curve using the time at which it was obtained as identified in data field 250. When a reference curve is selected, an indication is made in data field 250 and that functional residual capacity curve is displayed as the reference curve 252. Curve 252 shows a lung that is not well ventilated. Further indication of the reference curve and reference curve values may be made by a color indication for this data, different from that of the other functional residual capacity data in graph 110 and table 112. The result is a visual indicator that can easily be referred to by the clinician to quickly assess improvement or deterioration in the functional residual capacity condition of patient 12 over time. In the example shown in FIG. 5, there has been an increase in the functional residual capacity of patient 12 for each eight hour interval.

Also, it is common practice to alter, usually increase, the PEEP to improve ventilation of lungs 38 of patient 12 by opening areas of the lung that are not being properly ventilated. Tabulating the actual measured values for PEEPe and PEEPi, along with the corresponding functional residual capacity determination, as shown in FIG. 5, allows the clinician to see the effect, if any of applied PEEPe therapy on the volume of the functional residual capacity of the patient's lungs, as well as on the intrinsic PEEP. As also shown in FIG. 5, a history of a certain number of functional residual capacity determinations and PEEP pressures are shown in table 112 to present trends and the history of these quantities. In the example shown there, an increase in PEEPe has resulted in an increase in functional residual capacity of patient 12.

FRC Events Log

Certain clinical or other events can affect the value for functional residual capacity determined from the method steps shown in FIG. 7. Such events may include performing a suction routine on patient 12 to remove accumulated secretions, administering a nebulized medication, changing the ventilation mode, or changing one or more ventilation parameters, such as tidal volume (TV), breath rate, PEEP, or other parameter.

By selecting the FRC Log field 253 in menu 108 of screen 102g2 shown in FIG. 5, screen 102g4 of FIG. 8 will be shown to provide a log of the events that may effect functional residual capacity in data field 254 along with the time(s) and date(s) the event took place. The log also includes the time, date and value of any periodic functional residual capacity determinations made in the manner described above. The clinician may scroll through the events of the log using control knob 106 to review the functional residual capacity event history in relation to the measured values of functional residual capacity to determine if specific actions had a positive or negative effect on the determined functional residual capacity for the patient.

Trends Log Display

Figure 11:
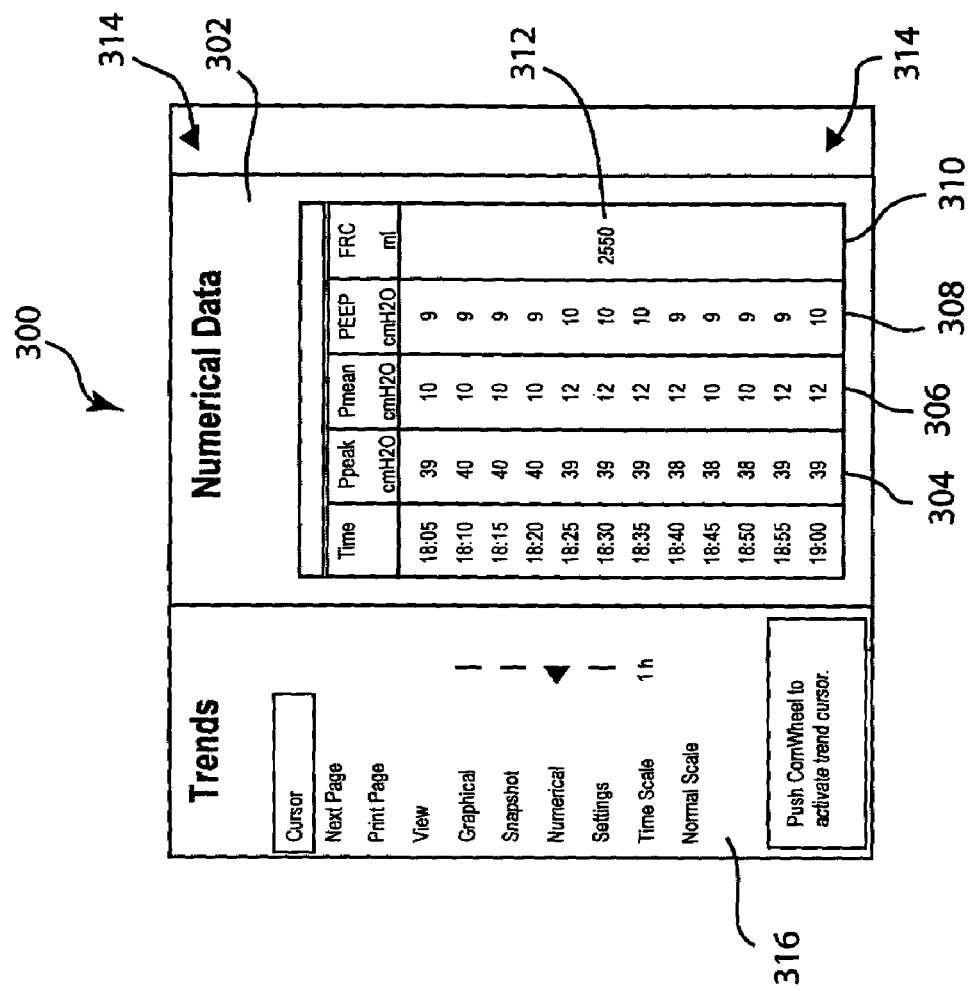
FIG. 11 shows a tabular display displaying fictional residual capacity values with periodically obtained ventilator operating data and/or patient condition data.
Figure 12:
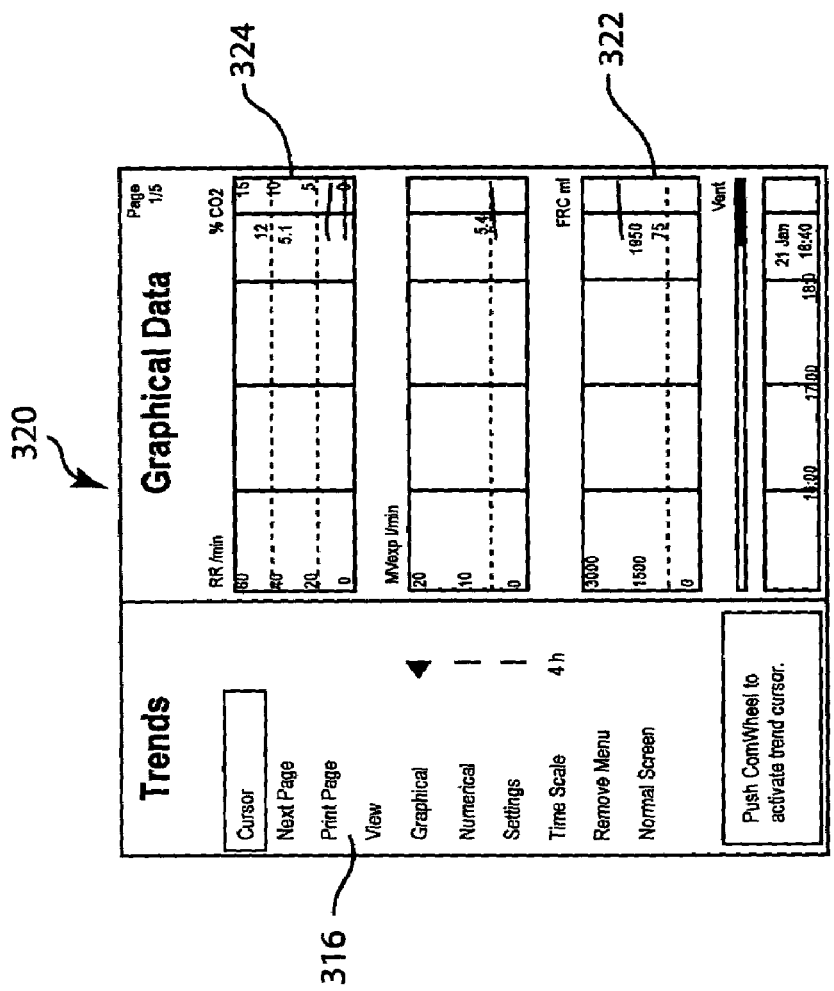
FIG. 12 shows a graphic display displaying functional residual capacity values with periodically obtained ventilator operating data and/or patient condition data.

The functional residual capacity value(s) determined in the above manner can also be provided in conjunction with a tabular and/or graphic display of periodic ventilator operating data and/or patient condition data, as shown in FIGS. 11 and 12. For example, the display may show ventilator and/or patient data existing at points of time spaced at five minute intervals. Such a display is helpful in documenting and identifing trends in the treatment and condition of the patient over time and hence is termed a "Trends" log.

A tabular trends log 300 is shown in FIG. 11 showing numerical data values obtained at five minute intervals for a period of an hour in tabulation field 302. The data columns exemplarily show a plurality of airway pressure conditions in columns 304, 306 and 308, including PEEP in column 308. As functional residual capacity determinations become available, they can be entered in the trends tabulation in column 310, as at 312.

While tabulation field shows data for one hour, data for a much longer period, such as 14 days, may be stored in a memory in ventilator 10 or display unit 76. Cursor 314 allows the clinician to scroll through the stored data to display data from a desired time period. Tabulation field 302 is accompanied by an appropriate menu 316 operable by control knob 106 for selecting desired data to be shown and other properties of the trends log display.

FIG. 12 shows a graphical trends log display 320 in which functional residual capacity data 322 is graphically shown for a period of time, such as three hours, along with other data from ventilator 10 or patient 12, such as respiratory rate (RR) 324. The same menu 316 may be used with this display.

The trends log displays may be placed in screen portion 102g by actuating an appropriate button in display unit 76 such as vent setup button 73 or spirometry button 75.

Spirometry Display

It may also be helpful for the clinician to have a better idea of how much of an increase in functional residual capacity is due to distension of the lung by increased PEEP and how much is due to making previously closed alveolar sacs available, i.e., opening of the lung by "recruitment" of lung volume. Such information can be obtained using the spirometry aspects of the present invention, as shown in the SpiroD screen 102g3 of FIG. 9.

In general, spirometry is used to determine the mechanics of a patient's lungs by examining relationships between breathing gas flows, volumes, and pressures during a breath of a patient. A commonly used relationship is that between inspired/expired breathing gas flows and volumes that, when graphed, produces a loop spirogram. The size and shape of the loop is used to diagnose the condition of the lung.

A relationship also exists between inspired/expired gas volumes and pressure in the lungs. In the past, a problem with the use of this relationship has been that pressure has been measured at a point removed from the lungs so that the measured pressure may not be an accurate reflection of actual pressure in the lungs thus lessening the diagnostic value of the pressure-volume loop. Through the use of catheter 94 extending from endotracheal tube 90 shown in FIG. 2, a far more accurate indication of lung pressure is obtained. For a healthy lung, a graph of the relationship between volume and pressure is roughly an elongated, narrow loop of positive uniform slope. That is, constant increments of inspired volume increase lung pressure by constant increments. The loop is formed because there remains some amount of lung resistance below the pressure sensing point at the end of catheter 94. In a diseased lung, the loop may be wider and may also reflect a non-linear lung volume pressure relationship. For such a lung, the volume-pressure relationship over the course of an inspiration/expiration may be in a form such as that shown in FIG. 9 by 420, and a curve illustrating the volume-pressure relationship resulting from a mathematical computation using loop data is plotted, as shown in FIG. 9 by reference numeral 422. The curve 422 shown in FIG. 9 in often termed a "dynostatic curve" and is used for diagnostic purposes. A typical dynostatic curve is shown in FIG. 9 to contain a middle portion of somewhat linear positive slope and a pair of inflection points separating end portions of differing slopes. The dynostatic curve and its generation is described in Practical Assessment of Respiratory Mechanics by Ola Stenqvist, British Journal of Anesthesia 91(1), pp.

92-105 (2003) and "The Dynostatic Algorithm in Adult and Paediatric Respiratory Monitoring" by Soren Sondergaard, Thesis, University Hospital, Gothenburg University, Sweden (2002).

In graph 110 of FIG. 9, the abscissa of the graph is lung pressure measured at the end of catheter 94 connected to the auxiliary input A of ventilator display unit 76 and is termed "Paux". The ordinate is scaled in volume of breathing gases inspired/expired by patient 12. It will be appreciated that this volume comprises the tidal volume for the patient. The tidal volume moves into and out of the lungs in a manner that can be described as being "above" the functional residual capacity. That is, for normal breathing, a patient starts a breath with the volume of the lungs at the functional residual capacity which may, for example be 2000 ml. During inhalation, the volume of the lungs increases by the tidal volume of, for example 500-700 ml, and during exhalation, the volume of the lungs decreases by approximately that amount. The same situation occurs when a patient is being provided with breathing gases from a mechanical ventilator, such as ventilator 10. It must thus be appreciated that the ordinate of the graph 110 in FIG. 9 is scaled in the relative volume of inspiration/expiration for which the origin of the graph is zero, not in absolute volume that would also take into consideration functional residual capacity and for which the origin of a graph would be the amount of the functional residual capacity. The scaling of graph 110 of FIG. 9 may be automatically altered to provide a scale appropriate to the spiromety data being shown.

With PEEP applied to patient 12 by ventilator 10, there will be a movement of the graph away from the origin of the axes along the abscissa. The graph will move right by the amount of the PEEP, i.e. the lung pressure at the end of expiration by patient 12.

The menu portion 108 of SpiroD screen 102g3 shown in FIG. 9 allows the user to open up a set up menu, shown in FIG. 10 that allows the clinician to turn a purge flow through catheter 94 on or off to zero the Paux sensor connected to catheter 94 when the purge flow is on and endotracheal tube 90 has been inserted in patient 12. The SpiroD set-up menu also allows the clinician to set the scaling for the graphical portions of the display. A "Paux Alarm" screen, reached from the SpiroD setup screen of FIG. 10, allows the clinician to set appropriate alarms for patient lung pressure, as sensed by catheter 94.

Various other selections on menu 108 of screen 102g3 of FIG. 9 allow the clinician to save the current data and to view this information as a first or second reference for use and display with subsequently obtained data. Up to a given number of loops, for example, six loops and curves, may be saved for analytical purposes. The "erase reference" option allows the user to determine which information to save and which to delete.

The "SpiroD loops" and "SpiroD curves" menu items may be turned on or off. Selecting "on" for both the curve and loop will display both the loop and the curve at once in the manner shown in FIG. 9. For easier comparison among loops and curves obtained at various times, either the loop or curve showing may be turned "off." The "cursor" option allows the clinician to scroll along the horizontal axis and display the actual pressure and volume measurements associated with the loops or curves that are displayed.

For the graphical showing of graph 110 of the screen 102g3 in FIG. 9, volumes and pressures are obtained from sensor 57 and catheter 94 and the spirometry data, computed and displayed for every third breath if the respiratory rate is less than some desired number, for example, 15 breaths per minute. If the respiratory rate is greater than that number, every fifth breath used. The loop 420 for a complete inspiratory/expiratory breathing cycle is displayed in the graph of screen 102g3 of FIG. 9. The dynostatic curve 422 is then calculated for display in graph 110.

Various compliance values for the patient's lungs are shown in the table 112 of screen 102g3 of FIG. 9. Compliance can be seen as the amount by which the volume of the lung increases for an incremental increase in lung pressure. The data necessary to determine compliance can be obtained from sensor 57 and gas module 64. Compliance is represented by the slope of dynostatic curve 422. It is an indication of the stiffness or elasticity of the lung. In a stiff lung, an incremental increase in pressure results in a smaller increase in volume over a lung that is more elastic and the slope of the curve 422 is more horizontal. In an elastic lung, the reverse is true. To aid the clinician in analyzing the lungs of patient 10, the compliance is computed at the beginning, middle, and end of the respiratory cycle of the patient. As shown in the example in FIG. 9, the middle portion of dynostatic curve 422 indicates a portion of greater compliance than the end portions. The table of the screen sets out numerical values. Ordinarily, the highly compliant, middle portion of curve 422 shown in FIG. 9 is that in which the lung is most effectively ventilated.

The table 112 of display 102g3 of FIG. 9 also shows the peak pressure achieved in the lungs during the breath, the PEEP pressure, and the airway resistance, Raw. The airway resistance is the pressure drop experienced by breathing gas flow of the lungs and is expressed in units of pressure per unit of flow. Airway resistance can also be determined with data from sensor 57 and gas module 64 in a manner described in the Stenqvist reference noted above.

Various alternatives and embodiments are contemplated as being within the scope of the following claims particularly pointing out and distinctly claiming the subject matter regarded as the invention.

What is claimed is:

1. A ventilator for ventilating a patient and for carrying out a determination of the functional residual capacity of the patient, said ventilator being couplable to a breathing circuit having a gas monitor and delivering/receiving breathing gases to/from the patient, said ventilator comprising:

at least one gas flow control valve and controller for providing breathing gases containing oxygen and an inert gas to the breathing circuit for delivery to the patient; and for causing the ventilator to alter the amount of oxygen in the breathing gases provided to the breathing circuit and patient;

a central processing unit incorporated in said ventilator for controlling said ventilator, said central processing unit employing the amount of inert gas expired by the patient obtained from measurements by the gas monitor following alteration of the amount of oxygen in the breathing gases to determine the functional residual capacity of the patient; and a display coupled to said central processing unit for displaying information relating to the operation of the ventilator and the determined functional residual capacity.

2. The ventilator according to claim 1 wherein said central processing unit determines the functional residual capacity of the patient at the conclusion of each breath in a series of breaths.

3. The ventilator according to claim 2 wherein said display provides a graphic display of the functional residual capacity determined for each breath in a series of breaths as it is determined.

4. The ventilator according to claim 3 wherein said display provides a graph comprising a plot of functional residual capacity values and breath number.

5. The ventilator according to claim 2 wherein said display provides a table of breath numbers and functional residual capacity values.

6. The ventilator according to claim 1 wherein said display displays the determined functional residual capacity at the end of a series of breaths in tabular form.

7. The ventilator according to claim 1 wherein said at least one gas flow control valve and controller restores the amount of oxygen to an original level following the determination of functional residual capacity and wherein said control processing unit determines functional residual capacity when breathing gases of altered oxygen content are provided to the patient and thereafter determines functional residual capacity when breathing gases having the restored level of oxygen content are provided to the patient.

8. The ventilator according to claim 7 wherein said central processing unit determines the functional residual capacity of the patient at the conclusion of each breath of a series of breaths.

9. The ventilator according to claim 8 wherein said display provides a graphic display of the functional residual capacity sequentially determined for each breath of a series of breaths during the provision of breathing gases of altered oxygen content and during the provision of breathing gases having the restored level of oxygen content.

10. The ventilator according to claim 3 including a memory for storing earlier determinations of functional residual capacity and wherein said display graphically displays same, as a reference curve, with subsequent functional residual capacity determinations.

11. The ventilator according to claim 9 wherein said central processing unit determines functional residual capacity after each breath in a series of breaths and wherein said ventilator includes a memory for storing earlier determinations of functional residual capacity and wherein said display graphically displays same, as a reference curve, with subsequent functional residual capacity determinations.

12. The ventilator according to claim 7 wherein said display displays two values of functional residual capacity in tabular form if the difference in value for the two determinations of functional residual capacity is in excess of a predetermined amount.

13. The ventilator according to claim 1 wherein said display tabulates the functional residual capacity determination.

14. The ventilator according to claim 13 wherein said display tabulates the functional residual capacity determination with values of PEEPe and PEEPi.

15. The ventilator according to claim 2 wherein said display is further defined as providing a graphic display of the functional residual capacity determinations and wherein said graphic display has auto scaling.

16. The ventilator according to claim 1 wherein said display is further defined as tabulating the functional residual capacity determinations along with changes in ventilator settings and/or procedures that affect functional residual capacity, thereby to provide a functional residual capacity log.

17. The ventilator according to claim 1 wherein said display is further defined as displaying functional residual capacity determinations in conjunction with periodically obtained data of the operation of the ventilator and/or the ventilation of the patient.

18. The ventilator according to claim 17 wherein said display is further defined as displaying the information in tabular form.

19. The ventilator according to claim 17 wherein said display is further defined as displaying the information in graphic form.

20. The ventilator according to claim 1 wherein said at least one gas flow control valve and controller and said central processing unit terminate the provision of breathing gases with altered oxygen and the determination of functional residual capacity responsive to predetermined conditions or changes in the operation of the ventilator and/or predetermined conditions or changes in the treatment or ventilation of the patient.

21. The ventilator according to claim 1 further including control means for causing said at least one gas flow control valve and controller and said central processing unit to carry out their operation to determine functional residual capacity at periodic intervals.

22. The ventilator according to claim 21 wherein said control means is further defined as altering the periodic determination of functional residual capacity responsive to action by a clinician, to a predetermined event or circumstance, or to a change in ventilation setting.

23. The ventilator according to claim 21 wherein said display tabulates the functional residual capacity determinations.

24. The ventilator according to claim 23 wherein said display tabulates the functional residual capacity determination with PEEPe and PEEPi.

25. A ventilator according to claim 1 having means for generating and storing spirometry data of the breaths of a patient and means for generating spirometry data for a breath including a loop of lung pressure and tidal volume data and a dynostatic curve obtained from the loop, said display displaying the spirometry data.

26. A ventilator according to claim 25 wherein said display displays spirometry data for a plurality of breaths and the ventilator includes means for turning on/off the loops and/or curves of the spirometry data.

27. The ventilator according to claim 25 wherein said display has auto scaling.

28. A method for ventilating a patient with a ventilator and for carrying out a determination of the functional residual capacity of the patient, the ventilator being couplable to a breathing circuit having a gas monitor and delivering/receiving breathing gases to/from the patient, said method comprising the steps of:
  (a) providing breathing gases containing oxygen and an inert gas to the breathing circuit for delivery to the patient;
  (b) causing the ventilator to alter the amount of oxygen in the breathing gases provided to the breathing circuit and patient;
  (c) obtaining the amount of inert gas expired by the patient from measurements by the gas monitor following alteration of the amount of oxygen in the breathing gases;
  (d) determining the functional residual capacity of the patient based on the alteration in the amount of oxygen and the amount of expired inert gas using a central processing unit incorporated in the ventilator for controlling the ventilator; and
  (e) displaying the determined functional residual capacity and information relating to the operation of the ventilator.

29. The method according to claim 28 wherein step (d) is further defined as determining the functional residual capacity of the patient at the conclusion of each breath of a series of breaths.

30. The method according to claim 29 wherein step (d) is further defined as determining the functional residual capacity over a predetermined number of breaths.

31. The method according to claim 29 wherein step (d) is further defined as terminating the determination of the functional residual capacity when the functional residual capacity measurement has become stable.

32. The method according to claim 31 further defined as including the step of measuring the composition of the breathing gases expired by the patient to determine when to terminate the determination of the functional residual capacity.

33. The method according to claim 29 wherein step (e) is further defined as providing a graphic display of the sequential functional residual capacity determinations for the breaths of a series of breaths.

34. The method according to claim 29 wherein step (e) is further defined as providing a graph comprising a plot of functional residual capacity and breath number.

35. The method according to claim 28 wherein step (e) is further defined as displaying the determined functional residual capacity at the end of a series of breaths in tabular form.

36. The method according to claim 28 wherein step (b) is further defined as causing the ventilator to provide one of an increase or decrease in the amount of oxygen in the breathing gases and thereafter restoring the amount of oxygen to an original level and wherein step (d) is further defined as determining functional residual capacity when breathing gases of increased or decreased oxygen content are provided to the patient and when breathing gases having the restored level of oxygen content are provided to the patient.

37. The method according to claim 29 wherein step (b) is further defined as causing the ventilator to provide one of an increase or decrease in the amount of oxygen in the breathing gases and thereafter restoring the amount of oxygen to an original level and wherein step (d) is further defined as determining functional residual capacity when breathing gases of increased or decreased oxygen content are provided to the patient and when breathing gases having the restored level of oxygen content are provided to the patient.

38. The method according to claim 33 including step (f) of storing earlier determinations of functional residual capacity and displaying same, as a reference curve, with subsequent functional residual capacity determinations.

39. The method according to claim 36 wherein step (e) is further defined as displaying two values of functional residual capacity in tabular form if the difference in values for the two determinations of functional residual capacity is in excess of a predetermined amount.

40. The method according to claim 28 wherein step (e) is further defined as tabulating the functional residual capacity determination.

41. The method according to claim 40 wherein step (e) is further defined as tabulating the functional residual capacity data with PEEPe and PEEPi.

42. The method according to claim 29 wherein step (e) is further defined as displaying the determined functional residual capacity as a graph having auto scaling.

43. The method according to claim 28 wherein step (e) is further defined as tabulating functional residual capacity determinations along with changes in ventilator settings and/or procedures that affect functional residual capacity, thereby to provide a functional residual capacity log.

44. The method according to claim 28 wherein step (e) is further defined as displaying functional residual capacity determination in conjunction with periodically obtained data of the operation of the ventilator and/or ventilation of the patient.

45. The method according to claim 44 wherein step (e) is further defined as displaying in tabular form.

46. The method according to claim 44 wherein step (e) is further defined as displaying in graphic form.

47. The method according to claim 28 wherein steps (b) and (d) are further defined as terminating the provision of breathing gases with altered oxygen and the determination of functional residual capacity responsive to predetermined conditions or changes in the operation of the ventilator and/or predetermined conditions or changes in the treatment or ventilation of the patient.

48. The method according to claim 28 further defined as repeating steps (b), (c), and (d) to determine functional residual capacity at periodic intervals.

49. The method according to claim 48 further defined as altering the periodic determination of functional residual capacity responsive to action by a clinician, to a predetermined event or circumstance, or to a change in ventilation setting.

50. The method according to claim 48 wherein step (e) is further defined as tabulating the functional residual capacity determinations.

51. The method according to claim 50 wherein step (e) is further defined as tabulating the functional residual capacity data with PEEPe and PEEPi.

52. A method for producing a display of functional residual capacity determinations and events affecting the functional residual capacity of a patient receiving mechanical ventilation, said method comprising the steps of:
   determining the functional residual capacity of the patient at a sequence of points in time;
   identifying the occurrence of selected events affecting the functional residual capacity of the patient including their nature and time of occurrence;
   correlating the determinations of functional residual capacity and the event occurrences;
   storing the determinations of functional residual capacity and event occurrences; and
   displaying a chronological listing of functional residual capacity determinations and natures of functional residual capacity affecting events as a log.

53. The method of claim 52 wherein the selected events include actions relating to patient treatment and a change in ventilator setting.

* * * * *